United States Patent [19]
Tiffin

[11] Patent Number: 6,087,495
[45] Date of Patent: Jul. 11, 2000

[54] PROCESS FOR THE PREPARATION OF GALANTHAMINE

[75] Inventor: Peter David Tiffin, Cambridge, United Kingdom

[73] Assignee: Janssen Pharmaceutica, N.V., Belgium

[21] Appl. No.: 09/101,174

[22] PCT Filed: Jan. 6, 1997

[86] PCT No.: PCT/GB97/00023

§ 371 Date: Jul. 2, 1998

§ 102(e) Date: Jul. 2, 1998

[87] PCT Pub. No.: WO97/25330

PCT Pub. Date: Jul. 17, 1997

[30] Foreign Application Priority Data

Jan. 4, 1996 [GB] United Kingdom ............... 9600080

[51] Int. Cl.$^7$ .................................................. C07D 491/08
[52] U.S. Cl. ............................................................ 540/581
[58] Field of Search ............................... 564/409; 540/581

*Primary Examiner*—Samuel Barts
*Attorney, Agent, or Firm*—Saliwanchik, Lloyd & Saliwanchik

[57] ABSTRACT

The subject invention concerns a process for the preparation of enantiomerically-enriched galanthamine from racemic galanthamine, and a process for increasing the enantiomeric excess of enantiomerically-enriched galanthamine, by direct crystallization of galanthamine salts.

18 Claims, No Drawings

PROCESS FOR THE PREPARATION OF GALANTHAMINE

This application is a 371 of PCT/GB97/00023 filed filed Jan. 6, 1997.

FIELD OF THE INVENTION

This invention relates to processes for the manufacture of enantiomerically-enriched forms of galanthamine, in free base or salt form.

BACKGROUND TO INVENTION (−)-Galanthamine and derivatives thereof are useful compounds for the treatment of Alzheimer's disease and related illnesses. Currently galanthamine is usually obtained by extraction from natural sources, such as daffodil or snowdrop bulbs. However, the yields of these extractive procedures are low, resulting in high costs and limited supplies of naturally obtained galanthamine.

It is known that single enantiomer galanthamine (2) can be prepared from racemic narwedine (1) through resolution followed by reduction of the enone function, as depicted in Scheme 1, below. Usefully, since the enantiomers of narwedine (1) readily equilibrate (racemise) by way of reversible ring opening to a dienone, coupled to the fact that crystals of racemic (1) exist as a conglomerate of enantiomers, a dynamic resolution of (1) can be carried out by crystallisation with entrainment by crystals of the desired isomer (see Barton and Kirby, J. Chem. Soc. (C) (1962) 806). However, in respect of a total synthesis, racemic narwedine itself is not readily available.

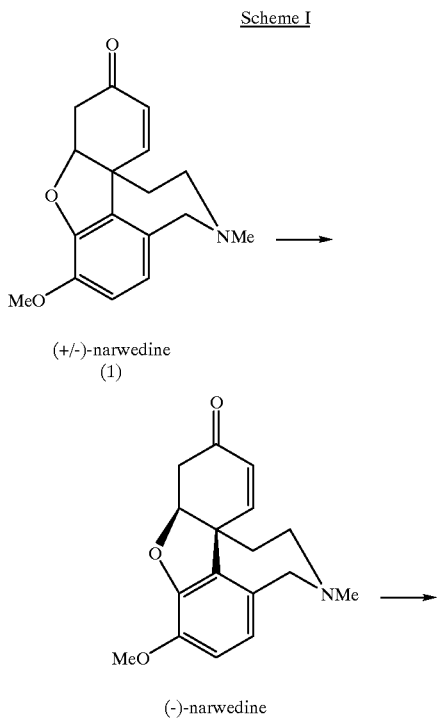

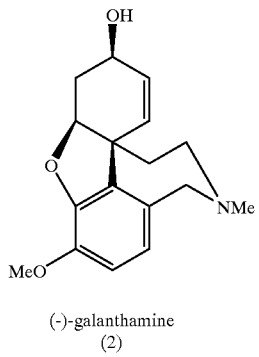

Several procedures have been developed for the resolution of galanthamine. One procedure involves formation of a diastereomeric salt with di-p-toluoyl tartaric acid and separation of the mixture by recrystallisation; see Kametani et al, Heterocycles, 1976, 1111. However, the need for the unnatural form of tartaric acid to access the desired, therapeutically-active, (−)-galanthamine renders this process costly.

Another resolution procedure involves the formation of diastereomeric esters with (−)-camphanic chloride and separation of the mixture by recrystallisation; see Szewczyk et al, J Het. Chem. (1995) 32: 195. The resultant product is then converted into (−)-galanthamine by reduction in a process which destroys the chiral auxiliary group, so rendering this process impractical for economic production.

SUMMARY OF THE INVENTION

The present invention is based on the surprising discovery of processes for the separation of the enantiomers of galanthamine by direct crystallisation techniques.

According to a first aspect of the present invention, a process for the preparation of an enantiomerically-enriched galanthamine salt, in which the counterion is achiral, comprises seeding a supersaturated solution of the racemic salt with an enantiomerically-enriched form of the salt, and recovering the salt form that crystallises out of solution.

According to a second aspect of the present invention, a process for increasing the enantiomeric excess of an enantiomerically-enriched galanthamine salt, in which the counterion is achiral, comprises crystallisation of a solution of the said enantiomerically-enriched salt, and recovery of the salt form that crystallises out of solution. Optionally, the solution can be seeded with an enantiomerically-enriched form of the salt. Advantageously, this process for enhancing enantiomeric enrichment can be used subsequent to any process capable of producing enantiomerically-enriched galanthamine, to achieve very high enantiomeric excess.

Both the processes of the present invention have the advantage of simplicity and cost effectiveness. Preferably, the processes are employed to manufacture salt forms enriched in (−)-galanthamine, which can then be used directly in pharmaceutical formulations, provided of course that the salt counterion is pharmaceutically-acceptable, or converted to the free base form of galanthamine, eg. by reaction with an appropriate base. However, both processes can adequately be used to prepare salt forms enriched in (+)-galanthamine, or the free base thereof, if this is desired.

DESCRIPTION OF THE INVENTION

In the context of the present Application, by enantiomerically-enriched typically we mean at least 10% ee, more typically at least 20% ee, upto what may be considered substantially single enantiomer form, for instance at least 80% ee, and typically at least 90% ee, or higher.

The salt used in the present invention can be any salt which is capable of giving the desired result. Preferably, the salt is pharmaceutically-acceptable, thereby allowing direct incorporation into pharmaceutical formulations, as mentioned above. Most preferably, the salt is the hydrogen bromide salt, as this is the form in which (−)-galanthamine is currently marketed.

Without being bound by theory, it seems that racemic galanthamine hydrobromide exists as a conglomerate of its enantiomers rather than the more common case where racemates crystallise in space groups containing both enantiomeric forms. Evidence for the presence of a conglomerate is that the racemate and the pure enantiomer have identical IR spectra; see Jacques, Enantiomers, Racemates and Resolutions, Krieger, Fla., 1991, p 53. Furthermore, (−)-galanthamine hydrobromide shows much lower solubility than racemic hydrobromide salt in methanol, their respective solubilities being 6 mg/ml and 17 mg/ml. Processes for the separation of conglomerates are well described in the literature (see, for instance, Crosby, chirality in Industry, Wiley, Chichester, 1992 p 24–27).

The racemic galanthamine salt for use in the process according to the first aspect of the present invention can be manufactured using standard chemical techniques, in which racemic galanthamine is reacted with a moiety providing the salt counterion. Racemic galanthamine can be made by, for instance, reduction of racemic narwedine. The enantiomerically-enriched salt employed as the seed in the crystallisation process can be prepared from enantiomerically-enriched galanthamine obtained from natural sources, or from other synthetic procedures, as only a small amount of this is required. The enantiomeric excess of the seed is preferably high, for instance at least 90% ee, or higher, ie. substantially single enantiomer form.

To a degree, the enantiomeric excess that is obtained is dependent upon the process conditions employed, with optimisation of conditions such as temperature, concentration and solvent allowing higher enantiomeric excess to be achieved.

The process according to the second aspect of the invention can be used to increase the enantiomeric excess of enantiomerically-enriched material obtained by way of the process according to the first aspect of the invention, or by any other method for preparing enantiomerically-enriched galanthamine, such as classical resolution or reduction of racemic or enantiomerically-enriched narwedine, and conversion to the appropriate salt form. Examples of classical resolution procedures have been given above. Reduction of (−)-narwedine can be carried out using any suitable reducing agent, such as lithium aluminium hydride as described by Barton and Kirby, although this has the disadvantage that epigalanthamine is also formed, or L-Selectride, although this reagent tends to be expensive and is only available in pilot plant quantities. Asymmetric reduction of racemic narwedine is described in WO-A-9631453, also in the name of the present Applicant.

Optionally, a seed can be added to aid crystallisation. The seed should be enriched in the desired enantiomer, to direct the crystallisation to that enantiomer. The enantiomeric excess of the seed can be the same as or different to that of the salt solution to which it is added, but preferably it is of high enantiomeric excess, eg. at least 90% ee, or higher.

The increases in enantiomeric excess that are possible using this process again depend to a degree on process condition optimisation, but can be up to 50% ee or more, providing at least 90% ee, preferably at least 98% ee, or higher, in the final product.

The processes of the invention may be applicable to galanthamine derivatives also.

The present invention is now illustrated by way of the following Examples. Example 1 illustrates the process according to the first aspect of the present invention, and Examples 2 to 5 the process according to the second aspect of the invention.

EXAMPLE 1

Racemic galanthamine hydrobromide (101 mg) was dissolved in methanol (4.5 ml) at 60° C. and the solution allowed to cool to 20° C. Seed crystals of (−)-galanthamine hydrobromide (1 mg) were added and the mixture stirred at 20° C. for 4 hours. The mixture was filtered to afford (−)-galanthamine hydrobromide (17 mg) with an enantiomeric excess of 19%.

EXAMPLE 2

(−)-Galanthamine (6.11 g, 68% ee) was dissolved in EtOH (18 ml) by warming to 35° C. 48% HBr (3 ml, 1.2 equiv.) in EtOH (3 ml) was added, giving a white precipitate. After cooling in ice the solid was collected by filtration. Yield=6.01 g, (77%), 90% ee.

5.0 g of the (−)-galanthamine.HBr salt obtained was dissolved in $H_2O$ (10 ml) on heating. (−)-Galanthamine.HBr seed crystals (3 mg) were added and the mixture cooled to room temperature. The resulting solid was collected by filtration. Yield=1.7 g (34%), >98% ee.

EXAMPLE 3

(−)-Galanthamine.HBr (3.0 g)(90% ee) was slurried in EtOH (30 ml) at reflux. After 60 min. the mixture was cooled to room temperature, and stirred for 16 hours. Filtration yielded (−)-galanthamine.HBr (2.28 g, 76%) of >98% ee.

EXAMPLE 4

(−)-Galanthamine (18.0 g, 81% ee) was dissolved in EtOH (65 ml) by warming. 48% HBr (8.4 ml) in EtOH (10 ml) was added dropwise. The resulting white solid was collected by filtration. Yield=22.06 g (96%).

This solid was dissolved in 3:1 $IMS:H_2O$ (200 ml) on heating to reflux, and then cooled to 5° C. giving a white solid. Recovery of the solid yielded (−)-galanthamine.HBr (17.34 g, 79%), of >99.5% ee.

EXAMPLE 5

(−)-Galanthamine (41.5 g, 44% ee) was dissolved in EtOH (170 ml). 48% HBr (19.4 ml) in EtOH (20 ml) was added dropwise to the solution, giving a white precipitate. This was collected by filtration. Yield of (−)-galanthamine.HBr=48.7 g, 91%.

This material was recrystallised from 3:1 $IMS:H_2O$ to give a white solid. Yield=28.8 g (54%), of 92% ee.

I claim:

1. A process for the preparation of an enantiomerically-enriched galanthamine salt, in which the counterion is achiral, comprising seeding a supersaturated solution of the racemic salt with an enantiomerically-enriched form of the salt, and recovering the salt form that crystallises out of solution.

2. The process according to claim 1, for the preparation of a salt enriched in the (−)-enantiomer, wherein seeding is with a salt form enriched in the (−) enantiomer.

3. The process according to claim 1, for the preparation of a salt enriched in the (+)-enantiomer, wherein seeding is with a salt form enriched in the (+)-enantiomer.

4. A process for increasing the enantiomeric excess of a first enantiomerically-enriched galanthamine salt, in which the counterion is achiral, comprising crystallisation of a solution of the said first enantiomerically-enriched salt, and recovery of the salt form that crystallises out of solution.

5. The process according to claim 4, wherein the solution is enriched in the (−)-enantiomer of the salt.

6. The process according to claim 4, wherein the solution is enriched in the (+)-enantiomer of the salt.

7. The process according to claim 1, further comprising seeding the salt solution with a second enantiomerically-enriched form of the salt, enriched in the desired enantiomer.

8. The process according to claim 4, wherein the said first enantiomerically-enriched salt is prepared by a process as defined in claim 1.

9. The process according to claim 4, wherein the said first enantiomerically-enriched salt is prepared by classical resolution of racemic galanthamine, and conversion to the salt form.

10. The process according to claim 4, wherein the said first enantiomerically-enriched salt is prepared by asymmetric reduction of racemic narwedine to give enantiomerically-enriched galanthamine, and conversion to the salt form.

11. The process according to claim 4, wherein the said first enantiomerically-enriched salt is prepared by reduction of enantiomerically-enriched narwedine to give enantiomerically-enriched galanthamine, and conversion to the salt form.

12. The process according to claim 4, wherein the salt is the hydrobromide.

13. A process for preparing enantiomerically-enriched galanthamine, comprising forming an enantiomerically-enriched galanthamine salt using a process according to any preceding claim, and converting the salt to galanthamine.

14. The process according to claim 13, for preparing galanthamine enriched in the (−)-enantiomer, comprising forming the salt by a process as defined in claim 2.

15. The process according to claim 13, for preparing galanthamine enriched in the (+)-enantiomer, comprising forming the salt by a process as defined in claim 3.

16. The process according to claim 1, wherein the salt is the hydrobromide.

17. The process according to claim 13, for preparing galanthamine enriched in the (−)-enantiomer, comprising forming the salt by a process as defined in claim 5.

18. The process according to claim 13, for preparing galanthamine enriched in the (+)-enantiomer, comprising forming the salt by a process as defined in claim 6.

* * * * *